United States Patent [19]
Yamashita et al.

[11] Patent Number: 5,981,522
[45] Date of Patent: Nov. 9, 1999

[54] TREATMENT OF DISEASE CAUSED BY INFECTION OF HELICOBACTER

[75] Inventors: Katsuji Yamashita; Takehiko Yamane; Shinichi Sakashita, all of Kobe; Kazunori Hosoe, Takasago; Kenji Fujii, Akashi; Yasuhiro Saka, Kobe, all of Japan

[73] Assignee: Kaneka Corporation, Osaka, Japan

[21] Appl. No.: 09/041,821

[22] Filed: Mar. 12, 1998

Related U.S. Application Data

[62] Continuation-in-part of application No. 08/988,779, Dec. 11, 1997, abandoned, which is a continuation-in-part of application No. 08/817,935, filed as application No. PCT/JP96/02464, Aug. 29, 1996, abandoned.

[30] Foreign Application Priority Data

Sep. 1, 1995 [JP] Japan ................... 7-225317
Sep. 1, 1995 [JP] Japan ................... 7-225318
Feb. 28, 1997 [JP] Japan ................... 9-046753

[51] Int. Cl.$^6$ .................................................. A61K 31/54
[52] U.S. Cl. ..................................... 514/224.5; 514/229.5
[58] Field of Search ............................. 514/224.5, 229.5

[56] References Cited

U.S. PATENT DOCUMENTS

| | | |
|---|---|---|
| 4,086,225 | 4/1978 | Marsili et al. . |
| 4,341,785 | 7/1982 | Marchi et al. . |
| 4,690,919 | 9/1987 | Yamane et al. . |
| 5,352,679 | 10/1994 | Ferrieri et al. . |
| 5,476,669 | 12/1995 | Borody . |
| 5,478,819 | 12/1995 | Tarpilla et al. . |
| 5,629,297 | 5/1997 | McColm . |

FOREIGN PATENT DOCUMENTS

| | | |
|---|---|---|
| 0 190 709 A1 | 8/1986 | European Pat. Off. . |
| 0 366 914 A2 | 5/1990 | European Pat. Off. . |
| 0 787 494 A1 | 8/1997 | European Pat. Off. . |
| 59-231092 | 12/1984 | Japan . |
| WO97/02021 | 1/1997 | WIPO . |
| WO97/02039 | 1/1997 | WIPO . |

OTHER PUBLICATIONS

Calvin M. Kunin, Clinical Infectious Diseases (Suppl. I); pp. S3–S14, 1966.
PCT International Search Report for EP98103481 dated Nov. 19, 1996.
Database WPI Section Ch. Week 9123, XP002070959 & JP 03101681A, Apr. 26, 1991.
Database WPI Section Ch. Week 8506, XP002070960 & JP 59231092, Dec. 25, 1984.
Drug Evaluation "Rifaximin", Drugs vol. 49 No. 3, pp. 467–484, 1995.
Antimicrobial Agents and Chemotherapy, vol. 38 No. 5, pp. 1118–1122 May 1994.
Journal of Antimicrobial Chemotherapy, vol. 35, No. 4, pp. 545–549, Apr. 4, 1995.

*Primary Examiner*—Raymond Henley, III
*Attorney, Agent, or Firm*—Armstrong, Westerman, Hattori, McLeland & Naughton

[57] ABSTRACT

A method for treating a digestive organ disease caused by the infection of Helicobacter, comprising administering a rifamycin derivative expressed by the formula (I), or a physiologically acceptable salt thereof

1 Claim, No Drawings

TREATMENT OF DISEASE CAUSED BY INFECTION OF HELICOBACTER

This application is a continuation-in-part of application Ser. No. 08/988,779, filed Dec. 11, 1997, now abandoned, which is a continuation-in-part of application Ser. No. 08/817,935, filed Apr. 30, 1997, now abandoned, which is a § 371 national phase of international application PCT/JP96/02464, filed Aug. 29, 1996.

BACKGROUND OF THE INVENTION

The present invention relates to a medicine and a method for a medical treatment for diseases caused by the infection of *Helicobacter plori*. More particularly, it relates to a curative medicine and a method for a medical treatment for maladies of digestive organs such as gastritis, gastroduodenitis, erosive gastritis, gastric erosion, erosive duodenitis, gastric ulcer, duodenal ulcer and so on, which are caused by the infection of *Helicobacter plori* which is difficult to be eradicated by antibacterial agents such as usual antibiotic substances, synthetic antibacterial chemicals, and so on.

Nowadays it is known that the infection of *Helicobacter plori* onto a gastric epithelium of human being is a main factor for proceeding to either gastritis, gastric ulcer or duodenal ulcer and this is a possible factor for proceeding to stomach cancer. It is revealed that the relapse of gastric ulcer or duodenal ulcer is remarkably depressed by eradication of *Helicobacter plori* infecting to digestive, and various kinds of medicines, which are mainly antibacterial chemicals are tried to eradicate the bacteria For instance, bismuth medicines of which examples are colloidal bismuth subcitrate, bismuth subsalicylate and so on, antibacterial chemicals of which examples are amoxicillin, ampicillin, clarithromycin, ofloxacin, tetracycline and so on, antiprotozoals of which examples are tinidazole, metronidazole and so on, proton pump inhibitors of which examples are omeprazole, lansoprazole and so on, are tried to be administered alone or in combination with two or three kinds thereof. However, for high eradicative effect on the bacteria, it is necessary to use a combination of the plural medicines, because it is not sufficient to use the medicine alone for that purpose. Further it is known that some strains of *Helicobacter plori* separated from clinical samples have resistance to usual medicines, and it is desired to develop a new medicine which is made effective for an improved eradication of the bacteria and can be applied to the remedy for eradicating the bacteria of more patients.

SUMMARY OF THE INVENTION

As the result of an extensive study of the present inventors to develop new medicines for *Helicobacter plori*, they have eventually found that rifamycin derivatives expressed by the following formula (I) have high antibacterial activity to *Helicobacter pylori*, and thus they have completed the present invention.

Specifically the present invention provides a curative medicine for a digestive organ disease caused by the infection of Helicobacter comprising as an effective component a rifamycin derivative expressed by the formula (I), or a physiologically acceptable salt thereof:

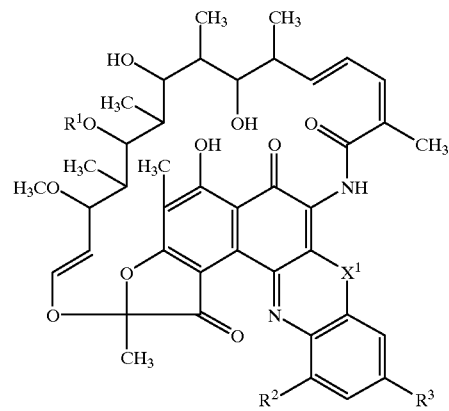

wherein $X^1$ represents an oxygen atom or a sulfur atom, $R^1$ represents an acetyl group or a hydrogen atom, $R^2$ represents a hydroxy group, a hydrogen atom, or an alkyl group having 1 to 3 carbon atoms, $R^3$ represents a group expressed by the formula:

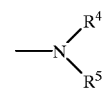

wherein $R^4$ and $R^5$ are the same or different and each is an alkyl group having 1 to 3 carbon atoms or

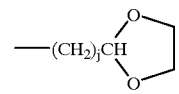

in which j represents an integer between 1 and 3; or a group expressed by the formula:

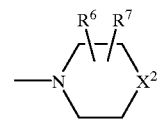

wherein $R^6$ and $R^7$ are the same or different and each is a hydrogen atom or an alkyl group having 1 to 3 carbon atoms, $X^2$ represents an oxygen atom, a sulfur atom, a carbonyl group,

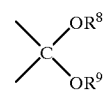

in which $R^8$ and $R^9$ are the same or different and each is a hydrogen atom, an alkyl group having 1 to 3 carbon atoms, or $R^8$ and $R^9$, in combination with each other, represent —$(CH_2)_k$— in which k represents an integer between 1 and 4, or

in which m represents 0 or 1, $R^{10}$ represents a hydrogen atom, an alkyl group having 1 to 6 carbon atoms or —$(CH_2)_nX^3$ in which n represents an integer between 1 and 4, and $X^3$ represents an alkoxy group having 1 to 3 carbon atoms, a vinyl group, an ethynyl group, or

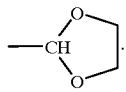

Further the present invention provides use of a rifamycin derivative expressed by the formula (I) or a physiologically acceptable salt thereof for the production of a curative medicine for a digestive organ disease caused by the infection of Helicobacter.

Furthermore the present invention provides a method for treating a digestive organ disease caused by the infection of Helicobacter comprising administering a rifamycin derivative expressed by the formula (I) or a physiologically acceptable salt thereof.

DETAILED DESCRIPTION

In the formula (I) mentioned above, each of the alkyl groups having 1 to 3 carbon atoms expressed by $R^2$, $R^4$, $R^5$, $R^6$, $R^7$, $R^8$ and $R^9$ can be a methyl group, an ethyl group, a propyl group, an isopropyl group and a cyclopropyl group. The alkyl group having 1 to 6 carbon atoms expressed by $R^{10}$ can be a chain or cyclic alkyl group, examples of which may be a methyl group, an ethyl group, a propyl group, an isopropyl group, a cyclopropyl group, a butyl group, an isobutyl group, a sec-butyl group, a tert-butyl group, a cyclobutyl group, a cyclopropylmethyl group, a pentyl group, an isopentyl group, a sec-pentyl group, a tert-pentyl group, a cyclopentyl group, a cyclobutylmethyl group, a hexyl group, a 4-methylpentyl group, a cyclohexyl group, a 3-methylcyclopentyl group and so on.

The alkoxy group having 1 to 3 carbon atoms expressed by $X^3$ can be a methoxy group, an ethoxy group, a propoxy group, an isopropoxy group and a cyclopropoxy group.

The rifamycin derivatives expressed by the formula (I), which are provided as a curative medicine for diseases caused by the infection of *Helicobacter plori*, can be synthesized by the following methods.

That is, the rifamycin derivatives can be synthesized by the methods disclosed in Examined Japanese Patent Publication JP-B-3-58352, Examined Japanese Patent Publication JP-B-5-57275, Unexamined Japanese Patent Publication JP-A-3-7291, Unexamined Japanese Patent Publication JP-A-4-103589, Unexamined Japanese Patent Publication JP-A-3-101689, Chem. Pharm. Bull., 41, 148 (1993) and so on. Further, the rifamycin derivatives can be synthesized by the methods disclosed in Preparation Examples of this specification Among the rifamycin derivatives expressed by the formula (I), the compounds in which $R^1$, $R^2$ and $R^3$ are the same as defined above, and $X^1$ represents a sulfur atom, can be synthesized by the following method. That is, the compounds can be obtained by reacting a compound expressed by the following formula (II) with a compound expressed by $HR^3$ wherein $R^3$ is the same as defined above in an aprotic polar solvent such as N,N-dimethylformamide, N,N-dimethylacetamide or dimethyl sulfoxide.

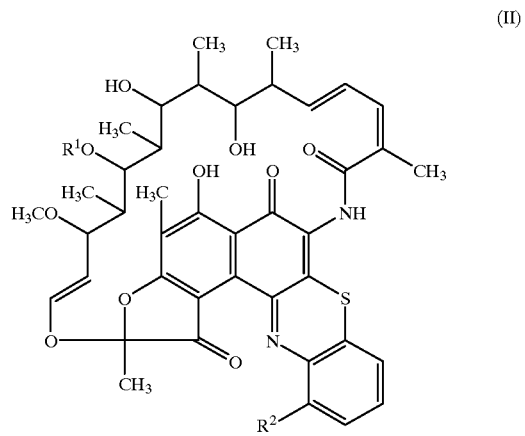

wherein $R^1$ and $R^2$ are the same as defined above.

Among the rifamycin derivatives expressed by the formula (I), the compounds in which $R^1$, $R^2$ and $X^1$ are the same as defined above, and $R^3$ is a group expressed by the formula:

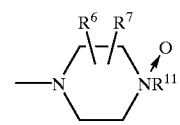

wherein $R^{11}$ represents an alkyl group having 1 to 6 carbon atoms or a group expressed by the formula: —$(CH_2)_nX^3$ in which n and $X^3$ are the same as defined above, and $R^6$ and $R^7$ are the same as defined above, can be synthesized by the following methods. That is, the compounds can be synthesized by oxidizing a compound expressed by the following formula (III):

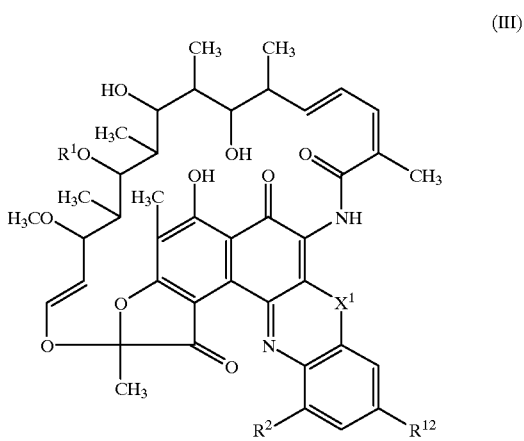

wherein $R^{12}$ represents a group expressed by the formula:

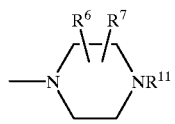

wherein $R^6$, $R^7$ and $R^{11}$ are the same as defined above, and $X^1$, $R^1$ and $R^2$ are the same as defined above, by (1) oxidation method using a hypohalite such as sodium hypochlorite or patassium hypobromite, (2) oxidation method using ozone, (3) oxidation method using hydroperoxide such as tert-butyl hydroperoxide or tert-amyl hydroperoxide, wherein a metallic catalyst such as vanadium or molybdenum may be allowed to coexist, (4) oxidation method using hydrogen peroxide, or (5) oxidation method using an organic peracid such as performic acid or peracetic acid. When the method (4) using hydrogen peroxide is selected among the oxidation methods, the desired product can be obtained in high selectivity and yield.

The compounds can also be obtained by reacting a compound expressed by the following formula (IV):

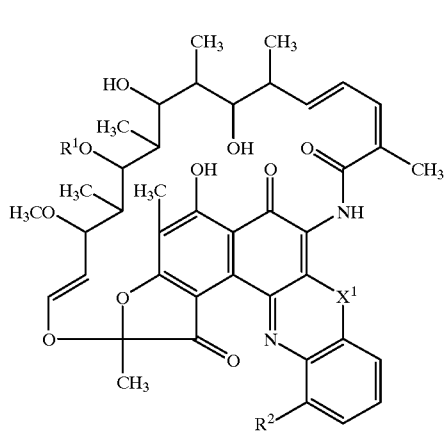

(IV)

wherein $X^1$, $R^1$ and $R^2$ are the same as defined above, with a compound expressed by the formula: $HR^{13}$ wherein $R^{13}$ prepresens a group expressed by the formula:

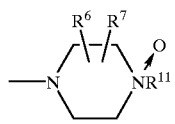

wherein $R^6$, $R^7$ and $R^{11}$ are the same as defined above, in an aprotic polar solvent such as N,N-dimethylformamide, N,N-dimethylacetamide or dimethyl sulfoxide.

Among the rifamycin derivatives expressed by the formula (I), the compounds in which $R^1$ is hydrogen atom can be obtained by hydrolyzing compounds of the formula (I) in which $R^1$ is acetyl group, by the method disclosed in Examined Japanese Patent Publication JP-B-5-57275.

The physiologically acceptable salts of the rifamycin derivatives which can be used as a curative medicine for diseases caused by the infection of *Helicobacter plori* can be available by selecting physiologically acceptable salts from the salts (salts with bases or acids) disclosed in the above-mentioned Japanese Patent Publications or the salts of the compounds disclosed in this specification.

Typical examples of the salts of the rifamycin derivatives with bases which can be used as a curative medicine for diseases caused by the infection of *Helicobacter plori* in accordance with the present invention are (1) metal salts, particularly salts with alkaline metals or alkali earth metals, (2) ammonium salts, and (3) amine salts, particularly salts with methylamine, ethylamine, diethylamine, triethylamine, pyrrolidine, morpholine, hexamethyleneimine, and the like. Typical examples of the salts with acids are (1) salts with mineral acids, for example, sulfuric acid and hydrochloric acid, (2) salts with organic acids, for example, p-toluenesulfonic acid, trifluoroacetic acid, acetic acid, and the like.

Assays of antibacterial activity were carried out in order to examine the activity of the rifamycin derivatives expressed by the formula (I) against *Helicobacter plori* which is a pathogenic bacterium for digestive organ diseases.

Assays of antibacterial activity of rifamycin derivatives expressed by the formula (I) were carried out by determination of minimal inhibitory concentration by agar plate dilution method using 5 strains (shown in Tables 1 and 2) and 10 strains (shown in Tables 3 and 4) of *Helicobacter pylori* obtained by separation from clinical samples. As a culture medium, 5% equine blood added blood agar culture medium No.2 (OXOID) was selected, and assayed compounds were added so that a desired concentration thereof was obtained. After inoculation, the assayed bacteria were incubated at 35° C. in 10% cabon dioxide gas concentration, and the antibacterial activity was determined after 72 hours comparing with the results obtained by using the sample without assayed compound as a control. The results are shown in Tables 1 to 4. $X^1$, $R^1$, $R^2$ and $R^3$ in Tables 1 to 4 correspond to those defined in the formula (I) mentioned above. In what follows, the derivatives correspond to those shown in Tables 1 to 4. $MIC_{80}$ is minimal inhibitory concentration (MIC) in which growth of 80% of strains used in the assay are inhibited, and is shown in unit of µg/ml.

From the results in Tables 1 to 4, it is clearly seen that the rifamycin derivatives expressed by the formula (I), which are used as a curative medicine for diseases caused by the infection of *Helicobacter plori* in accordance with the present invention, have extremely high antibacterial activity as compared with rifampicin which is a known rifamycin derivative used as antituberculosis agent.

TABLE 1

Antibacterial activity of the assayed compounds

| Derivative No. | $X^1$ | $R^1$ | $R^2$ | $R^3$ | $MIC_{80}$ (unit: µg/ml) |
|---|---|---|---|---|---|
| 1 | O | CH₃CO— | H | —N(CH₃)₂ | 0.031 |
| 2 | O | CH₃CO— | H | —N(piperazinyl)NCH₃ | 0.016 |

TABLE 1-continued

Antibacterial activity of the assayed compounds

| Derivative No. | $X^1$ | $R^1$ | $R^2$ | $R^3$ | $MIC_{80}$ (unit: μg/ml) |
|---|---|---|---|---|---|
| 3 | O | CH₃CO— | OH | —N(CH₃)—CH₂CH(1,3-dioxolan-2-yl) | 0.008 |
| 4 | O | CH₃CO— | OH | morpholino | 0.008 |
| 5 | O | CH₃CO— | OH | 3,5-dimethylpiperazin-1-yl | 0.063 |
| 6 | O | CH₃CO— | OH | 4-methylpiperazin-1-yl | 0.016 |
| 7 | O | CH₃CO— | OH | 4-ethylpiperazin-1-yl | 0.008 |
| 8 | O | CH₃CO— | OH | 4-propylpiperazin-1-yl | 0.004 |
| 9 | O | CH₃CO— | OH | 4-isopropylpiperazin-1-yl | 0.008 |
| 10 | O | CH₃CO— | OH | 4-isobutylpiperazin-1-yl | 0.016 |
| 11 | O | CH₃CO— | OH | 4-(1,3-dioxolan-2-ylmethyl)piperazin-1-yl | 0.016 |
| 12 | S | CH₃CO— | H | 4-methylpiperazin-1-yl | 0.063 |
| 13 | O | H | OH | 4-ethylpiperazin-1-yl | 0.063 |
| 14 | O | H | OH | 4-isobutylpiperazin-1-yl | 0.063 |
| Rifampicin | | | | | 1 |

TABLE 2

Antibacterial activity of the assayed compounds

| Derivative No. | $X^1$ | $R^1$ | $R^2$ | $R^3$ | $MIC_{80}$ (unit: μg/ml) |
|---|---|---|---|---|---|
| 15 | O | CH₃CO— | OH | thiomorpholino | 0.016 |
| 16 | O | CH₃CO— | OH | 4-(cyclopropylmethyl)piperazin-1-yl | 0.016 |
| 17 | O | CH₃CO— | OH | 4-butylpiperazin-1-yl | 0.063 |

TABLE 2-continued
Antibacterial activity of the assayed compounds
| Derivative No. | X¹ | R¹ | R² | R³ | MIC₈₀ (unit:μg/ml) |
|---|---|---|---|---|---|
| 18 | O | CH₃CO— | OH | 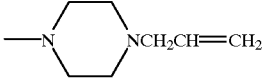 | 0.031 |
| 19 | O | CH₃CO— | OH | 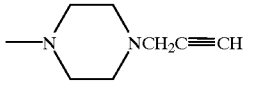 | 0.031 |
| 20 | O | CH₃CO— | OH |  | 0.031 |
| Rifampicin | | | | | 0.5 |
TABLE 3
Antibacterial activity of the assayed compounds
| Derivative No. | X¹ | R¹ | R² | R³ | MIC₈₀ (unit:μg/ml) |
|---|---|---|---|---|---|
| 21 | O | CH₃CO— | H | 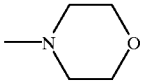 | 0.016 |
| 22 | O | CH₃CO— | H | 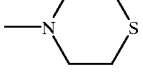 | 0.063 |
| 23 | O | CH₃CO— | H | 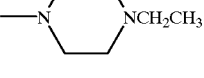 | 0.016 |
| 24 | O | CH₃CO— | H | 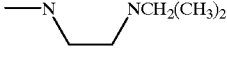 | 0.008 |
| 25 | O | CH₃CO— | H | 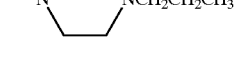 | 0.008 |
| 26 | O | CH₃CO— | H |  | 0.016 |
| 27 | O | CH₃CO— | H | 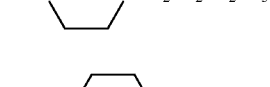 | 0.016 |
| 28 | O | CH₃CO— | H | 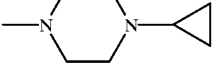 | 0.031 |

TABLE 3-continued

Antibacterial activity of the assayed compounds

| Derivative No. | $X^1$ | $R^1$ | $R^2$ | $R^3$ | $MIC_{80}$ (unit:μg/ml) |
|---|---|---|---|---|---|
| 29 | O | CH₃CO— | H | —N(piperazine)NCH₂CH=CH₂ | 0.008 |
| 30 | O | CH₃CO— | H | —N(2-methylpiperazine)NCH₃ | 0.008 |
| 31 | O | CH₃CO— | H | —N(2-methylpiperazine)NCH₂CH₃ | 0.016 |
| 32 | O | CH₃CO— | H | —N(2-methylpiperazine)NCH(CH₃)₂ | 0.016 |
| 33 | O | CH₃CO— | H | —N(2,6-dimethylpiperazine)NCH₃ | 0.016 |
| 34 | O | CH₃CO— | H | —N(2,6-dimethylpiperazine)NCH₂CH₃ | 0.031 |
| 35 | O | CH₃CO— | H | —N(2,6-dimethylpiperazine)NCH₂CH₂CH₃ | 0.016 |
| 36 | O | CH₃CO— | H | —N(3-methylpiperazine)NCH(CH₃)₂ | 0.016 |
| 37 | O | CH₃CO— | H | —N(3,5-dimethylpiperazine)NCH₃ | 0.063 |

TABLE 3-continued
Antibacterial activity of the assayed compounds
| Derivative No. | $X^1$ | $R^1$ | $R^2$ | $R^3$ | $MIC_{80}$ (unit:μg/ml) |
|---|---|---|---|---|---|
| 38 | O | CH₃CO— | H | 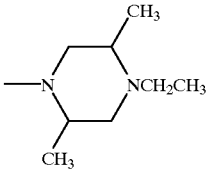 | 0.031 |
| 39 | O | CH₃CO— | H | 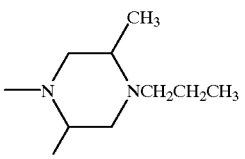 | 0.031 |
| Rifampicin | | | | | 1 |
TABLE 5
Antibacterial activity of the assayed compounds
| Derivative No. | $X^1$ | $R^1$ | $R^2$ | $R^3$ | $MIC_{80}$ (unit:μg/ml) |
|---|---|---|---|---|---|
| 40 | O | CH₃CO— | CH₃ | 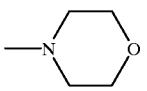 | 0.016 |
| 41 | O | CH₃CO— | H | 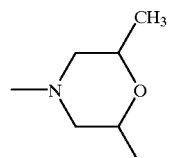 | 0.031 |
| 42 | O | CH₃CO— | H | 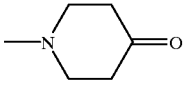 | 0.063 |
| 43 | O | CH₃CO— | CH₃ | 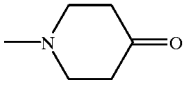 | 0.016 |
| 44 | O | CH₃CO— | H |  | 0.016 |
| 45 | O | CH₃CO— | CH₃ |  | 0.031 |

TABLE 5-continued

Antibacterial activity of the assayed compounds

| Derivative No. | $X^1$ | $R^1$ | $R^2$ | $R^3$ | $MIC_{80}$ (unit:μg/ml) |
|---|---|---|---|---|---|
| 46 | O | CH₃CO— | H | —N(piperidine-spiro-1,3-dioxolane) | 0.016 |
| 47 | O | CH₃CO— | CH₃ | —N(piperidine-spiro-1,3-dioxolane) | 0.031 |
| 48 | O | CH₃CO— | CH₃ | —N(piperazine)NCH₃ | 0.008 |
| 49 | O | CH₃CO— | CH₃ | —N(piperazine)NCH₂CH₃ | 0.008 |
| 50 | O | CH₃CO— | CH₃ | —N(piperazine)NCH(CH₃)₂ | 0.008 |
| 51 | O | CH₃CO— | CH₃ | —N(piperazine)NCH₂CH₂CH₃ | 0.008 |
| 52 | O | CH₃CO— | CH₃ | —N(piperazine)NCH₂CH₂CH₂CH₃ | 0.031 |
| 53 | O | CH₃CO— | CH₃ | —N(piperazine)NCH₂CH=CH₂ | 0.016 |
| 54 | O | CH₃CO— | CH₃ | —N(2,6-dimethylpiperazine)NCH₃ | 0.008 |
| Rifampicin | | | | | 1 |

With respect to derivative 55 obtained by oxidizing derivative 25 shown in Table 3 with hydrogen peroxide, assay of antibacterial activity was performed under the same conditions as above using 10 strains of *Helicobacter plori* obtained from clinical samples. It was found that $MIC_{80}$ of derivative 55 was 0.008 μg/ml. The result reveals that derivative 55 has a strong antibacterial activity.

Derivative 10 was evaluated for the eradicative effect on an animal whose stomach was infected with *Helicobacter pylori* in the following way.

Male jird (Mongolian gerbil) (MGS/sea) of 7 week-old were used as test animals. A bacterial suspension wherein the colony forming unit of *Helicobacter pylori* ATCC 43504 was adjusted in the range of $3 \times 10^8$ to $1 \times 10^9$/ml was orally administered in a dose of 0.5 ml /animal for three successive days, thereby preparing animals whose stomach was infected with *Helicobacter pylori*. The test for eradicative effect was performed using the stomach infected animals.

A dispersion of derivative 10 wherein derivative 10 was dispersed in an amount of 2 mg /ml or 4 mg /ml in a 0.1 mole/l citric acid buffer solution (pH 4.3) containing 2.5% gum arabic was administered to jirds in treated group in a dose of 10 mg derivative 10/kg per day or 20 mg derivative 10/kg per day, respectively, for 5 days from 16th day after the infection. As a reference for the treatment, a dispersion of clarithromycin, which is known as an agent for eradicating *Helicobacter pylori* and is used clinically as an eradicating agent, wherein clarithromycin is dispersed in an amount of 4 mg /ml in 2.5% gum arabic aqueous solution was administered in a dose of 20 mg clarithromycin/kg in the same manner as in the case of derivative 10. To jirds in untreated group was administered a 0.1 mole/l citric acid buffer solution (pH 4.3) containing 2.5% gum arabic in a dose of 5 ml/kg.

The eradicative effect of derivative 10 on animal whose stomach was infected with *Helicobacter pylori* was evaluated by comparison of the aforesaid 4 groups.

The stomach of each jird was enucleated 4 days after the completion of adminsitration of drugs. The stomach was homogenized together with 10 ml of a physiological saline solution by means of a homogenizer. The resulting homogenate was applied to a cluture medium wherein 10 mg /l vancomycin, 2,500 IU/l polymyxin, 2.5 mg/l trimethoprim 15 mg/l nalidixic acid and 3 mg/l amphotericin B were added to Skirrow culture medium and incubated under the same conditions as described in the aforesaid assay of antibacterial activity. The colony forming unit of *Helicobacter pylori* in the stomach was determined.

As a result, the colony forming unit of *Helicobacter pylori* in the stomach was $2.7 \times 10^5$/stomach on the average for 4 animals in one group in untreated group, and $4.2 \times 10^5$/stomach on the average for 3 animals in one group in clarithromycin-treated group. Thus, a clear eradicative effect was not observed in clarithromycin-treated group.

In derivative 10-treated groups, the colony forming unit of *Helicobacter pylori* in the stomach was smaller than $1 \times 10^3$/stomach, which value is the limit of detection, in all 4 animals in each group both in 10 mg/kg-treated group and in 20 mg/kg-treated group. These results reveal that *Helicobacter pylori* infected to stomach can be effectively eradicated by administration of derivative 10 and derivative 10 is more effective than clarithromycin which is known as an agent for eradicating *Helicobacter pylori*.

Derivatives 40, 49 and 51 were also evaluated for eradicative effect on *Helicobacter plori* infected jird in the same manner as in the above test for derivative 10. Each derivative was administered in a dose of 10 mg/kg per day for 5 days.

As a result, the colony forming unit of *Helicobacter pylori* in the stomach was $2.6 \times 10^6$/stomach on the average for 4 animals in untreated group. In contrast thereto, in derivative 40-treated group, the colony forming unit of *Helicobacter pylori* in the stomach was smaller than $1.0 \times 10^3$/stomach in one animal among three animals used in the test and $3.2 \times 10^4$/stomach on the average for the remaining two animals, which value was smaller than that in the untreated group. In derivative 49-treated group, the colony forming unit of *Helicobacter pylori* in the stomach was smaller than $1.0 \times 10^3$/stomach in three animals among four animals in one group and $5.7 \times 10^5$/stomach in the remaining one animal, which value was smaller than that in the untreated group. In derivative 51-treated group, the colony forming unit of *Helicobacter pylori* in the stomach was smaller than $1.0 \times 10^3$/stomach in one animal among four animals used in one group and $3.6 \times 10^5$stomach on the average for the remaining three animals, which value was smaller than that in the untreated group.

All the rifamycin derivatives, of which the antibacterial activity is shown in Tables 1 to 4, and derivative 55 have low toxicity, and the oral administration of each compound in a dose of 1,000 mg/kg to mice showed no toxicity.

The medicine of the present invention, the effective component of which is a rifamycin derivative expressed by the formula (I) or a physiologically acceptable salt thereof, is effective as a curative medicine for digestive organ diseases such as gastritis, gastroduodenitis, erosive gastritis, gastric erosion, erosive duodenitis, gastric ulcer, duodenal ulcer and so on, which are caused by the infection of *Helicobacter pylori* which is difficult to be eradicated by antibacterial agents such as usual antibiotic substances, synthetic antibacterial chemicals and so on.

The curative medicine for digestive organ diseases caused by the infection of Helicobacter, the effective component of which is a rifamycin derivative expressed by the formula (I) or a physiologically acceptable salt thereof in the present invention, can be orally administered in the form of a powder, tablets, capsules, sugar-coated tablets, granules, syrup and so on. As the carrier for the preparation of the digestive organ disease curative medicine in the present invention, organic or inorganic solids or liquids suitable for oral administration, which are usually inert pharmaceutical carriers, can be used. Typical examples of the carrier are crystalline cellulose, gelatin, lactose, starch, magnesium stearate, talc, vegetable or animal fat or oil, gum, polyalkylene glycol and so on. The proportion of the effective component mentioned above in the medicine can be varied in the range of 0.2 to 100% of the weight of the medicine. And the digestive organ disease curative medicine of the present invention can include other curative medicines for digestive organ diseases and other medicines, which are compatible with it. Needless to say, in this case, the rifamycin derivative expressed by the formula (I) or its physiologically acceptable salt in the present invention may not be a main component in that medicine.

The curative medicine for digestive organ diseases in the present invention is usually administrated in such an amount that the desired effect can be achieved without side-effects. Their actual dose should be determined by a doctor. Generally, however, the digestive organ disease curative medicine of the present invention is administered in a dose of 10 mg to 10 g, preferably 20 mg to 5 g, based on the amount of the effective component, per day for an adult. Further, the digestive organ disease curative medicine of the present invention can be adminstered in a unit dosage preparation containing 1 mg to 5 g, preferably 3 mg to 1 g of the effective component.

The present invention will be described in more detail with reference to the following Examples and Preparation Examples.

EXAMPLE 1

A mixture of 100 g of derivative 8 shown in Table 1, 55 g of lactose and 41 g of dry potato starch was kneaded with 20 ml of water. The mixture was pressed out through a screen of 16 mesh, and dried at 40° C. to be granulated. Then, the granules were uniformly mixed with 4 g of magnesium stearate and compressed into tablets by a conventional method to give tablets which contained 100 mg of derivative 8 in a 200 mg tablet.

EXAMPLE 2

Using derivative 4 instead of derivative 8 in Example 1, tablets which contained 100 mg of derivative 4 in a 200 mg tablet were prepared by the same method as in Example 1.

EXAMPLE 3

Using derivative 10 instead of derivative 8 in Example 1, tablets which contained 100 mg of derivative 10 in a 200 mg tablet were prepared by the same method as in Example 1.

EXAMPLE 4

Using derivative 24 instead of derivative 8 in Example 1, tablets which contained 100 mg of derivative 24 in a 200 mg tablet were prepared by the same method as in Example 1.

EXAMPLE 5

Using derivative 25 instead of derivative 8 in Example 1, tablets which contained 100 mg of derivative 25 in a 200 mg tablet were prepared by the same method as in Example 1.

EXAMPLE 6

Using derivative 29 instead of derivative 8 in Example 1, tablets which contained 100 mg of derivative 29 in a 200 mg tablet were prepared by the same method as in Example 1.

EXAMPLE 7

Using derivative 49 instead of derivative 8 in Example 1, tablets which contained 100 mg of derivative 49 in a 200 mg tablet were prepared by the same method as in Example 1.

EXAMPLE 8

Using derivative 50 instead of derivative 8 in Example 1, tablets which contained 100 mg of derivative 50 in a 200 mg tablet were prepared by the same method as in Example 1.

EXAMPLE 9

Using derivative 51 instead of derivative 8 in Example 1, tablets which contained 100 mg of derivative 51 in a 200 mg tablet were prepared by the same method as in Example 1.

EXAMPLE 10

Using derivative 54 instead of derivative 8 in Example 1, tablets which contained 100 mg of derivative 54 in a 200 mg tablet were prepared by the same method as in Example 1.

EXAMPLE 11

196 g of the granules which were prepared by the same method as in Example 1, were mixed with 4 g of magnesium stearate, and 200 mg portions of the resulting mixture was filled into No. 2 capsules to give hard capsules which contained 100 mg of derivative 8 in each capsule.

EXAMPLE 12

Using derivative 4 instead of derivative 8 in Example 11, hard capsules which contained 100 mg of derivative 4 in each capsule were prepared by the same method as in Example 11.

EXAMPLE 13

Using derivative 10 instead of derivative 8 in Example 11, hard capsules which contained 100 mg of derivative 10 in each capsule were prepared by the same method as in Example 11.

EXAMPLE 14

Using derivative 24 instead of derivative 8 in Example 11, hard capsules which contained 100 mg of derivative 24 in each capsule were prepared by the same method as in Example 11.

EXAMPLE 15

Using derivative 25 instead of derivative 8 in Example 11, hard capsules which contained 100 mg of derivative 25 in each capsule were prepared by the same method as in Example 11.

EXAMPLE 16

Using derivative 29 instead of derivative 8 in Example 11, hard capsules which contained 100 mg of derivative 29 in each capsule were prepared by the same method as in Example 11.

EXAMPLE 17

Using derivative 49 instead of derivative 8 in Example 11, hard capsules which contained 100 mg of derivative 49 in each capsule were prepared by the same method as in Example 11.

EXAMPLE 18

Using derivative 50 instead of derivative 8 in Example 11, hard capsules which contained 100 mg of derivative 50 in each capsule were prepared by the same method as in Example 11.

EXAMPLE 19

Using derivative 51 instead of derivative 8 in Example 11, hard capsules which contained 100 mg of derivative 51 in each capsule were prepared by the same method as in Example 11.

EXAMPLE 20

Using derivative 54 instead of derivative 8 in Example 11, hard capsules which contained 100 mg of derivative 54 in each capsule were prepared by the same method as in Example 11.

EXAMPLE 21

10.0 g of derivative 3, 84.0 g of lactose, 4.5 g of crystalline cellulose and 1.5 g of magnesium stearate were mixed well to give a powder which contained 100 mg of derivative 3 in 1 g of the powder.

EXAMPLE 22

Using derivative 6 instead of derivative 3 in Example 21, a powder which contained 100 mg of derivative 6 in 1 g of the powder was prepared by the same method as in Example 21.

EXAMPLE 23

Using derivative 9 instead of derivative 3 in Example 21, a powder which contained 100 mg of derivative 9 in 1 g of the powder was prepared by the same method as in Example 21.

The method for producing the rifamycin derivatives in the present invention will be described with reference to the following Preparation Examples. In the following Preparation Examples, thin-layer chromatography was carried out using silica gel as a carrier, $^1$H-NMR spectrum was measured in chloroform using tetramethylsilane as an internal standard and the position of the signals was expressed in ppm unit.

PREPARATION EXAMPLE 1 (Synthesis of derivative 23)

1.57 g of benzoxazinorifamycin [synthesized by the method described in Helv. Chim. Acta 56, 2369 (1973)] was dissolved in 3.35 ml of N,N-dimethylacetamide, and the mixture was heated up to 50° C. To the mixture were added 0.46 g of N-ethylpiperazine and 0.52 g of manganese dioxide and the reaction was continued at 50° C. for 14 hours. To dilute the reaction mixture, 30 ml of ethyl acetate was added. The solid in the reaction mixture was separated by filtration using diatomaceous earth as a filter aid and the residue on the funnel was rinsed with a small amount of ethyl acetate. The combined ethyl acetate filtrate and rinse was washed with 30 ml of hydrochloric acid (0.03 mole/l) once and with 30 ml portions of a saturated solution of sodium chloride twice, and dried over anhydrous magnesium sulfate. The obtained ethyl acetate solution was evaporated under reduced pressure to remove the solvent. The resulting crude product was purified by silica gel column chromatography using 6 g of Wakogel C-200® (registered trademark of silica gel for column chromatography made by WAKO PURE CHEMICAL INDUSTRIES CO., LTD.) and chloroform as eluent. Fractions containing the desired product were collected and evaporated to dryness under reduced pressure. The product was dissolved into 10 ml of ethyl acetate at 60° C. and 20 ml of hexane was added to the solution. The solution was cooled slowly to room temperature to crystallize a product. The yield was 0.50 g.

Thin-layer Chromatography:

Rf 0.26 blue spot (solvent: chloroform/methanol=95/5 volume ratio), Rf 0.04 blue spot (solvent: toluene/tert-butanol=9/1 volume ratio)

$^1$H-NMR:

The signals derived from the introduced N-ethylpiperazine: 1.14(CH$_2$C$\underline{H}_3$), 2.49(C$\underline{H}_2$CH$_3$), 2.60 (NCH$_2$C$\underline{H}_2$NCH$_2$CH$_3$), 3.53(NC$\underline{H}_2$CH$_2$NCH$_2$CH$_3$)

PREPARATION EXAMPLE 2 (synthesis of derivative 24)

Using 0.51 g of N-isopropylpiperazine instead of N-ethylpiperazine in Preparation Example 1, the reaction was continued for 16 hours under the same condition as in Preparation Example 1. After the reaction mixture was treated in the same manner as in Preparation Example 1, the ethyl acetate solution was evaporated to dryness under reduced pressure to give a crude product. After the crude product was dissolved into 5 ml of ethyl acetate, 15 ml of hexane was added to the solution. The solution was cooled slowly to room temperature to crystallize a product. The same crystallization process as above was performed once more. The obtained product was purified by silica gel column chromatography using 2 g of Wakogel C-200® and chloroform as eluent. Fractions containing the desired product were collected and evaporated to dryness under reduced pressure. The product was dissolved into 5 ml of ethyl acetate at 60° C. and 15 ml of hexane was added to the solution. The solution was cooled slowly to room temperature to crystallize a product. The yield was 0.44 g.

Thin-layer Chromatography:

Rf 0.32 blue spot (solvent: chloroform/methanol=95/5 volume ratio), Rf 0.10 blue spot (solvent: toluene/tert-butanol=9/1 volume ratio)

$^1$H-NMR:

The signals derived from the introduced N-isopropylpiperazine: 1.09(CH(C$\underline{H}_3$)$_2$), 2.67(NCH$_2$C$\underline{H}_2$NCH(CH$_3$)$_2$), 2.76(C$\underline{H}$(CH$_3$)$_2$), 3.52(NC$\underline{H}_2$CH$_2$NCH(CH$_3$)$_2$)

PREPARATION EXAMPLE 3 (synthesis of derivative 25)

Using 0.51 g of N-propylpiperazine instead of N-ethylpeperazine in Preparation Example 1, the reaction was continued for 15 hours under the same condition as in in Preparation Example 1. To the reaction mixture, 30 ml of ethyl acetate was added to dilute the mixture. The solid in the reaction mixture was separated by filtration using diatomaceous earth as a filter aid and the residue on the funnel was rinsed with a small amount of ethyl acetate. The combined ethyl acetate filtrate and rinse was evaporated under reduced pressure. The product was dissolved into 10 ml of ethyl acetate, and 30 ml of hexane was added dropwise to the solution with agitating to precipitate the desired product. The obtained crude product was purified by silica gel column chromatography using 3 g of Wakogel C-200® and chloroform as eluent. Fractions containing the desired product were collected and evaporated to dryness under reduced pressure. After the crude product was dissolved into 10 ml of ethyl acetate at 60° C., 16 ml of hexane was added to the solution. The solution was cooled slowly to room temperature to crystallize a product. The yield was 0.69 g.

Thin-layer Chromatography:

Rf 0.38 blue spot (solvent: chloroform/methanol=95/5 volume ratio), Rf 0.13 blue spot (solvent: toluene/tert-butanol=9/1 volume ratio)

$^1$H-NMR:

The signals derived from the introduced N-propylpiperazine: 0.95(CH$_2$CH$_2$C$\underline{H}_3$), 1.55(CH$_2$C$\underline{H}_2$CH$_3$), 2.37(C$\underline{H}_2$CH$_2$CH$_3$), 2.59(NCH$_2$C$\underline{H}_2$NCH$_2$CH$_2$CH$_3$), 3.53(NC$\underline{H}_2$CH$_2$NCH$_2$CH$_2$CH$_3$)

PREPARATION EXAMPLE 4 (synthesis of derivative 26)

Using 0.57 g of N-isobutylpiperazine instead of N-ethylpeperazine in Preparation Example 1, the reaction was continued for 16 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 30 g of Wakogel C-200® and toluene/tert-butanol=95/5 (volume ratio) as eluent. Fractions containing the desired product were collected and evaporated to dryness under reduced pressure. After the crude product was dissolved into 10 ml of ethyl acetate at 60° C., 30 ml of hexane was added to the solution The solution was cooled slowly to room temperature to crystallize a product. The same process of crystallization was carried out once again. After the obtained crystalline product was dissolved into 10 ml of toluene at 60° C., 10 ml of hexane was added to the solution. The solution was cooled slowly to room temperature to crystallize a product. The obtained product was purified by silica gel column chromatography using 2 g of Wakogel C-200® and toluene/tert-butanol=95/5 (volume ratio) as eluent. After the partially purified product was dissolved into 5 ml of toluene at 60° C., 8 ml of hexane was added to the solution. The solution was cooled slowly to room temperature to crystallize a product. The obtained crystalline product was purified by preparative layer chromatography using Silica Gel 60 (E. Merck Inc.), 200×200×2 mm, and chloroform/methanol=97/3 (volume ratio) as solvent. After the purified product was dissolved into 5 ml of toluene at 60° C., 15 ml of hexane was added to the solution. The solution was cooled slowly to room temperature to crystallize a product. The yield was 0.50 g.

Thin-layer Chromatography:

Rf 0.54 blue spot (solvent: chloroform/methanol=95/5 volume ratio), Rf 0.35 blue spot (solvent: toluene/tert-butanol=9/1 volume ratio)

$^1$H-NMR:

The signals derived from the introduced N-isobutylpiperazine: 0.93(CH$_2$CH(CH$_3$)$_2$), 1.68(CH$_2$C H(CH$_3$)$_2$), 2.14(CH$_2$CH(CH$_3$)$_2$), 2.55(NC H$_2$CH$_2$NCH$_2$CH(CH$_3$)$_2$), 3.52(NCH$_2$CH$_2$NCH$_2$CH(CH$_3$)$_2$)

PREPARATION EXAMPLE 5 (synthesis of derivative 27)

Using 0.57 g of N-butylpiperazine instead of N-ethylpiperazine in Preparation Example 1, the reaction was continued for 15 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 3 g of Wakogel C-200® and chloroform as eluent. Further, the product was purified by the same silica gel column chromatography as above except for using 6 g of Wakogel C-200®. Fractions containing the desired product were collected and evaporated to dryness under reduced pressure. After the product was dissolved into 10 ml of ethyl acetate at 60° C., 10 ml of hexane was added to the solution. The solution was cooled slowly to room temperature to crystallize a product. The yield was 0.74 g.

Thin-layer Chromatography:

Rf 0.44 blue spot (solvent: chloroform/methanol=95/5 volume ratio), Rf 0.19 blue spot (solvent: toluene/tert-butanol=9/1 volume ratio)

$^1$H-NMR:

The signals derived from the introduced N-butylpiperazine: 0.95(CH$_2$CH$_2$CH$_2$CH$_3$), 1.36 (CH$_2$CH$_2$CH$_2$CH$_3$), 1.53(CH$_2$CH$_2$CH$_2$CH$_3$), 2.40(C H$_2$CH$_2$CH$_2$CH$_3$), 2.59(NCH$_2$CH$_2$NCH$_2$CH$_2$CH$_2$CH$_3$), 3.52 (NCH$_2$CH$_2$NCH$_2$CH$_2$CH$_2$CH$_3$)

PREPARATION EXAMPLE 6 (synthesis of derivative 28)

Using 0.50 g of N-cyclopropylpiperazine instead of N-ethylpiperazine in Preparation Example 1, the reaction was continued for 22 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 30 g of Wakogel C-200® and toluene/tert-butanol=95/5 (volume ratio) as eluent. Fractions containing the desired product were collected and evaporated to dryness under reduced pressure. After the product was dissolved into 10 ml of toluene at 60° C., 10 ml of hexane was added to the solution. The solution was cooled slowly to room temperature to crystallize a product. The yield was 0.92 g.

Thin-layer Chromatography:

Rf 0.49 blue spot (solvent: chloroform/methanol=95/5 volume ratio), Rf 0.24 blue spot (solvent: toluene/tert-butanol=9/1 volume ratio)

$^1$H-NMR:

The signals derived from the introduced N-cyclopropylpiperazine:

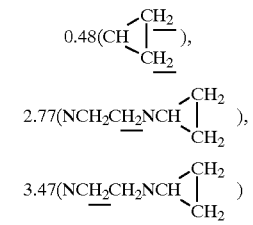

PREPARATION EXAMPLE 7 (synthesis of derivative 29)

Using 0.50 g of N-(2-propenyl)piperazine instead of N-ethylpiperazine in Preparation Example 1, the Example 1, the ethyl acetate solution was evaporated to dryness under reduced pressure to give a crude product. The obtained crude product was purified by silica gel column chromatography using 6 g of Wakogel C-200® and chloroform/methanol= 100/0 (volume ratio) to chloroform/methanol=95/5 (volume ratio) as eluent. Further, the obtained product was purified by silica gel column chromatography using 3 g of Wakogel C-200® and chloroform as eluent. Fractions containing the desired product were collected and evaporated to dryness under reduced pressure. After the product was dissolved into 4 ml of toluene at 60° C., 10 ml of hexane was added to the solution. The solution was cooled slowly to room temperature to crystallize a product. The yield was 0.74 g.

Thin-layer Chromatography:

Rf 0.40 blue spot (solvent: chloroform/methanol=95/5 volume ratio), Rf 0.15 blue spot (solvent: toluene/tert-butanol=9/1 volume ratio)

$^1$H-NMR:

The signals derived from the introduced N-(2-propenyl)piperazine: 2.61(NCH$_2$CH$_2$NCH$_2$CH=CH$_2$), 3.07(C H$_2$CH=CH$_2$), 3.52(NCH$_2$CH$_2$NCH$_2$CH=CH$_2$), 4.98,5.22 (CH$_2$CH=CH$_2$), 5.88(CH$_2$CH=CH$_2$)

PREPARATION EXAMPLE 8 (synthesis of derivative 30)

Using 0.46 g of 1,2-dimethylpiperazine instead of N-ethylpiperazine in Preparation Example 1, the reaction was continued for 16 hours under the same condition as in Preparation Example 1. After the reaction mixture was treated in the same manner as in Preparation Example 1, the ethyl acetate solution was evaporated to dryness under reduced pressure to give a crude product. The obtained crude product was twice purified by silica gel column chromatography using 3 g of Wakogel C-200® and chloroform as eluent. Fractions containing the desired product were collected and evaporated to dryness under reduced pressure. After the product was dissolved into 5 ml of toluene at 60° C., 10 ml of hexane was added to the solution. The solution was cooled slowly to room temperature to crystallize a product. The obtained crystalline product was purified by preparative layer chromatography using Silica Gel 60, 200× 200×2 mm, and chloroform/methanol=97/3 (volume ratio) as solvent. After the purified product was dissolved into 3 ml of toluene at 60° C., 10 ml of hexane was added to the solution. The solution was cooled slowly to room temperature to crystallize a product. The yield was 0.15 g.

Thin-layer Chromatography:

Rf 0.22 blue spot (solvent: chloroform/methanol=95/5 volume ratio), Rf 0.04 blue spot (solvent: toluene/tert-butanol=9/1 volume ratio)

$^1$H-NMR:

The signals derived from the introduced 1,2-dimethylpiperazine:

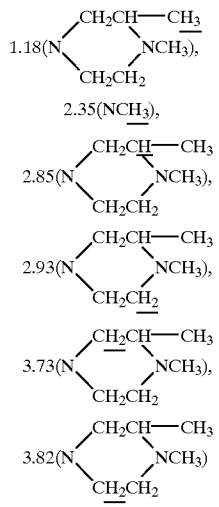

PREPARATAION EXAMPLE 9 (synthesis of derivative 31)

Using 0.51 g of 1-ethyl-2-ethylpiperazine instead of N-ethylpiperazine in Preparation Example 1, the reaction was continued for 21 hours under the same condition as in Preparation Example 1. After the reaction mixture was treated in the same manner as in Preparation Example 1, the ethyl acetate solution was evaporated to dryness under reduced pressure to give a crude product. The obtained crude product was purified twice by silica gel column chromatography using 3 g of Wakogel C-200® and chloroform as eluent. Fractions containing the desired product were collected and evaporated to dryness under reduced pressure. After the product was dissolved into 10 ml of ethyl acetate at 60° C., 30 ml of hexane was added to the solution. The solution was cooled slowly to room temperature to crystallize a product. The yield was 0.51 g.

Thin-layer Chromatography:

Rf 0.26 blue spot (solvent: chloroform/methanol=95/5 volume ratio), Rf 0.06 blue spot (solvent: toluene/tert-butanol=9/1 volume ratio)

$^1$H-NMR:

The signals derived from the introduced 1-ethyl-2-methylpiperazine:

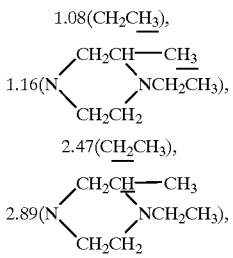

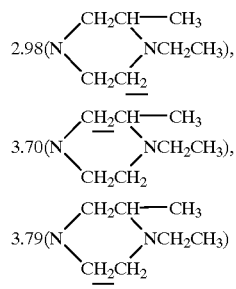

PREPARATION EXAMPLE 10 (synthesis of derivative 32)

Using 0.57 g of 1-isopropyl-2-methylpiperazine instead of N-ethylpiperazine in Preparation Example 1, the reaction was continued for 20 hours under the same condition as in Preparation Example 1. After the reaction mixture was treated in the same manner as in Preparation Example 1, the ethyl acetate solution was evaporated to dryness under reduced pressure to give a crude product. The obtained crude product was twice purified by silica gel column chromatography using 3.5 g of Wakogel C-200® and chloroform as eluent. Further the product was purified by silica gel column chromatography using 1.5 g of Wakogel C-200® and chloroform as eluent. Fractions containing the desired product were collected and evaporated to dryness under reduced pressure. After the product was dissolved into 5 ml of toluene at 60° C., 10 ml of hexane was added to the solution. The solution was cooled slowly to room temperature to crystallize a product. The yield was 0.37 g.

Thin-layer Chromatography:

Rf 0.32 blue spot (solvent: chloroform/methanol=95/5 volume ratio), Rf 0.13 blue spot (solvent: toluene/tert-butanol=9/1 volume ratio)

$^1$H-NMR:

The signals derived from the introduced 1-isopropyl-2-methylpiperazine:

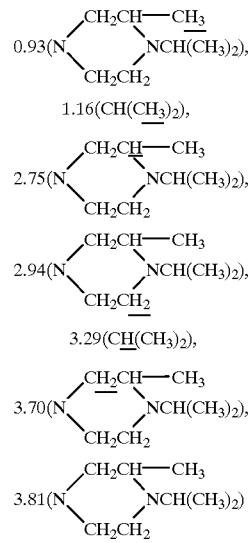

PREPARATION EXAMPLE 11 (synthesis of derivative 33)

Using 0.51 g of 1,2,6-trimethylpiperazine instead of N-ethylpiperazine in Preparation Example 1, the reaction was continued for 16 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 30 g of Wakogel C-200® and toluene/tert-butanol= 95/5 (volume ratio) as eluent. Fractions containing the desired product were collected and evaporated to dryness under reduced pressure. After the product was dissolved into 10 ml of ethyl acetate at 60° C., 10 ml of hexane was added to the solution. The solution was cooled slowly to room temperature to crystallize a product. The yield was 0.44 g.

Thin-layer Chromatography:

Rf 0.29 blue spot (solvent: chloroform/methanol=95/5 volume ratio), Rf 0.07 blue spot (solvent: toluene/tert-butanol=9/1 volume ratio)

$^1$H-NMR:

The signals derived from the introduced 1,2,6-trimethylpiperazine: 1.22(NCH$_2$CH(C$\underline{H}_3$)NCH$_3$), 2.32(NC$\underline{H}_3$), 2.88(NCH$_2$C$\underline{H}$(CH$_3$)NC$\underline{H}_3$), 3.76(NC$\underline{H}_2$CH(CH$_3$)NCH$_3$)

PREPARATION EXAMPLE 12 (synthesis of derivative 34)

Using 0.57 g of 2,6-dimethyl-1-ethylpiperazine instead of N-ethylpiperazine in Preparation Example 1, the reaction was continued for 14 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 3 g of Wakogel C-200® and chloroform as eluent. Fractions containing the desired product were collected and evaporated to dryness under reduced pressure. After the product was dissolved into 5 ml of ethyl acetate at 60° C., 15 ml of hexane was added to the solution and the solution was cooled slowly to room temperature to crystallize a product. The same crystallization process was conducted once more. Further the obtained crystalline product was purified by preparative layer chromatography using Silica Gel 60, 200×200×2 mm and chloroform/methanol=97/3 (volume ratio) as solvent. After the purified product was dissolved into 5 ml of toluene at 60° C., 15 ml of hexane was added to the solution. The solution was cooled slowly to room temperature to crystallize a product. The yield was 0.56 g.

Thin-layer Chromatography:

Rf 0.33 blue spot (solvent: chloroform/methanol=95/5 volume ratio), Rf 0.11 blue spot (solvent: toluene/tert-butanol=9/1 volume ratio)

$^1$H-NMR:

The signals derived from introduced 2,6-dimethyl-1-ethylpiperazine: 0.93(CH$_2$C$\underline{H}_3$), 1.20(NCH$_2$CH(C$\underline{H}_3$)NCH$_2$CH$_3$), 2.77(NC$\underline{H}_2$CH$_3$), 2.98(NCH$_2$C$\underline{H}$(CH$_3$)NCH$_2$CH$_3$), 3.76(NC$\underline{H}_2$CH(CH$_3$)NCH$_2$CH$_3$)

PREPARATION EXAMPLE 13 (synthesis of derivative 35)

Using 0.63 g of 2,6-dimethyl-1-propylpiperazine instead of N-ethylpiperazine in Preparation Example 1, the reaction was continued for 16 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 30 g of Wakogel C-200® and chloroform/methanol= 95/5 (volume ratio) as eluent. And the obtained partially purified product was purified by silica gel column chromatography using 6 g of Wakogel C-200° and chloroform as eluent, and further the same scale chromatography was performed using toluene instead of chloroform as eluent. The obtained partially purified product was purified by preparative layer chromatography using Silica Gel 60, 200× 200×2 mm and chloroform/methanol=95/5 (volume ratio) as solvent. A portion containing the desired product was scraped off and extracted with a solvent. The extract was evaporated to dryness. The yield was 0.23 g.

Thin-layer Chromatography:

Rf 0.40 blue spot (solvent: chloroform/methanol=95/5 volume ratio), Rf 0.18 blue spot (solvent: toluene/tert-butanol=9/1 volume ratio)

$^1$H-NMR:

The signals derived from the introduced 2,6-dimethyl-1-propylpiperazine: 0.86(NCH$_2$CH$_2$C$\underline{H}_3$), 1.19(NCH$_2$CH(C$\underline{H}_3$)NCH$_2$CH$_3$), 1.42(NCH$_2$C$\underline{H}_2$CH$_3$), 2.75(NC$\underline{H}_2$CH$_3$), 2.75(NCH$_2$C$\underline{H}$(CH$_3$)NC$\underline{H}_2$CH$_2$CH$_3$), 3.75 (NC$\underline{H}_2$CH(CH$_3$)NCH$_2$CH$_2$CH$_3$)

PREPARATION EXAMPLE 14 (synthesis of derivative 36)

Using 0.57 g of 1-isopropyl-3-methylpiperazine instead of N-ethylpiperazine in Preparation Example 1, the reaction was continued for 119 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 6 g of Wakogel C-200® and chloroform as eluent. Further the obtained partially purified product was purified three times by preparative layer chromatography using Silica Gel 60, 200×200×2 mm and chloroform/methanol= 95/5 (volume ratio) as solvent. A portion containing the desired product was scraped off and extracted with a solvent. The extract was evaporated to dryness. The yield was 0.29 g.

Thin-layer Chromatography:

Rf 0.47 blue spot (solvent: chloroform/methanol=95/5 volume ratio), Rf 0.29 blue spot (solvent: toluene/tert-butanol=9/1 volume ratio)

$^1$H-NMR:

The signals derived from the introduced 1-isopropyl-3-methylpiperazine:

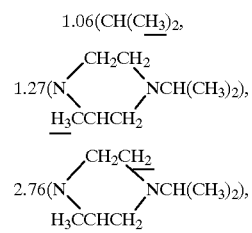

-continued 2.93(N⟨CH₂CH₂ / H₃CCHCH₂⟩NCH(CH₃)₂), 3.29(C<u>H</u>(CH₃)₂), 3.69(N⟨CH₂CH₂ / H₃CCHCH₂⟩NCH(CH₃)₂), 4.21(N⟨CH₂CH₂ / H₃CC<u>H</u>CH₂⟩NCH(CH₃)₂)

PREPARATION EXAMPLE 15 (synthesis of derivative 37)

Using 0.51 g of 1,2,5-trimethylpiperazine instead of N-ethylpiperazine in Preparation Example 1, the reaction was continued for 45 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 6 g of Wakogel C-200® and chloroform as eluent. Further the obtained partially purified product was purified by preparative layer chromatography using Silica Gel 60, 200×200×2 mm, and chloroform/methanol=95/5 (volume ratio) as solvent. The obtained partially purified product was purified by preparative layer chromatography using Silica Gel 60, 200×200×2 mm and chloroform/methanol=95/5 (volume ratio) as solvent. Further the product was purified twice by the same preparative layer chromatography using chloroform/methanol=90/10 (volume ratio) as solvent. A portion containing the desired product was scraped off and extracted with a solvent. The extract was evaporated to dryness. The yield was 0.24 g.

Thin-layer Chromatography:

Rf 0.26 blue spot (solvent: chloroform/methanol=95/5 volume ratio), Rf 0.08 blue spot (solvent: toluene/tert-butanol=9/1 volume ratio)

¹H-NMR:

The signals derived from the introduced 1,2,5-trimethylpiperazine:

1.03(N⟨CH₂C<u>H</u>—CH₃ / H₃CCHCH₂⟩NCH₃), 1.32(N⟨CH₂C<u>H</u>—CH₃ / H₃CCHCH₂⟩NCH₃), 2.36(NC<u>H</u>₃), 2.89(N⟨CH₂C<u>H</u>—CH₃ / H₃CCHCH₂⟩NCH₃), 3.01(N⟨CH₂CH—CH₃ / H₃CCHC<u>H</u>₂⟩NCH₃),

-continued 3.52(N⟨CH₂C<u>H</u>—CH₃ / H₃CCHCH₂⟩NCH₃), 4.13(N⟨CH₂CH—CH₃ / H₃CC<u>H</u>CH₂⟩NCH₃)

PREPARATION EXAMPLE 16 (synthesis of derivative 38)

Using 0.57 g of 2,5-dimethyl-1-ethylpiperazine instead of N-ethylpiperazine in Preparation Example 1, the reaction was continued for 67 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 3 g of Wakogel C-200® and toluene as eluent. The obtained partially purified product was purified twice by preparative layer chromatography using Silica Gel 60, 200× 200×2 mm and chloroform/methanol=90/10 (volume ratio) as solvent. Further the product was purified by the same preparative layer chromatography using chloroform/methanol=95/5 (volume ratio) as solvent. The obtained partially purified product was purified by silica gel column chromatography using 2 g of Wakogel C-200® and toluene as eluent. Fractions containing the desired product were collected and evaporated to dryness. The yield was 0.12 g.

Thin-layer Chromatography:

Rf 0.37 blue spot (solvent: chloroform/methanol=95/5 volume ratio), Rf 0.15 blue spot (solvent: toluene/tert-butanol=9/1 volume ratio)

¹H-NMR:

The signals derived from the introduced 2,5-dimethyl-1-ethylpiperazine:

0.97(N⟨CH₂CH—C<u>H</u>₃ / H₃CCHCH₂⟩NCH₂CH₃), 1.09(NCH₂C<u>H</u>₃), 1.33(N⟨CH₂C<u>H</u>—CH₃ / H₃CCHCH₂⟩NCH₂CH₃), 2.49(C<u>H</u>₂CH₃)

2.84(N⟨CH₂C<u>H</u>—CH₃ / H₃CCHCH₂⟩NCH₂CH₃), 3.01(N⟨CH₂CH—CH₃ / H₃CCHC<u>H</u>₂⟩NCH₂CH₃), 3.53(N⟨CH₂C<u>H</u>—CH₃ / H₃CCHCH₂⟩NCH₂CH₃),

-continued

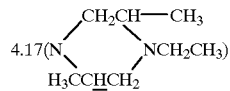
4.17(N⟨CH₂CH—CH₃ / NCH₂CH₃⟩ H₃CCH̲CH₂)

-continued

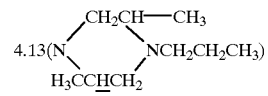
4.13(N⟨CH₂CH—CH₃ / NCH₂CH₂CH₃⟩ H₃CCH̲CH₂)

PREPARATION EXAMPLE 17 (synthesis of derivative 39)

Using 0.63 g of 2,5-dimethyl-1-propylpiperazine instead of N-ethylpiperazine in Preparation Example 1, the reaction was continued for 119 hours under the same condition as in Preparation Example 1. After the reaction mixture was treated in the same manner as in Preparation Example 1, the ethyl acetate solution was evaporated to dryness under reduced pressure to give a crude product. The obtained crude product was purified by silica gel column chromatography using 10 g of Wakogel C-200® and chloroform as eluent. The obtained partially purified product was purified by silica gel column chromatography using 3 g of Wakogel C-200® and chloroform as eluent. The obtained partially purified product was purified by preparative layer chromatography using Silica Gel 60, 200×200×2 mm and chloroform/methanol=95/5 (volume ratio) as solvent. Further the obtained product was purified by the same preparative layer chromatography using chloroform/methanol=98/2 (volume ratio) as solvent. A portion containing the desired product was scraped off and extracted with a solvent. The extract was evaporated to dryness. The yield was 0.21 g.

Thin-layer Chromatography:

Rf 0.51 blue spot (solvent: chloroform/methanol=95/5 volume ratio), Rf 0.31 blue spot (solvent: toluene/tert-butanol 9/1 volume ratio)

¹H-NMR:

The signals derived from the introduced 2,5-dimethyl-1-propylpiperazine:

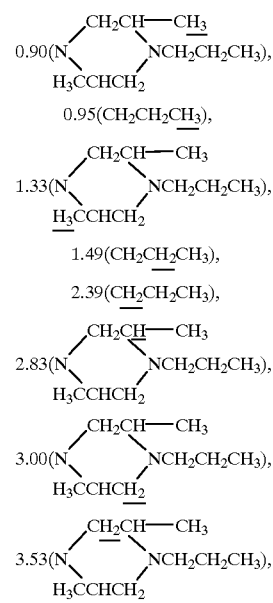

0.90(N⟨CH₂CH̲—CH₃ / NCH₂CH₂CH₃⟩ H₃CCHCH₂), 0.95(CH₂CH₂CH̲₃), 1.33(N⟨CH₂CH—CH₃ / NCH₂CH₂CH₃⟩ H₃CCHCH₂), 1.49(CH₂CH̲₂CH₃), 2.39(CH̲₂CH₂CH₃), 2.83(N⟨CH₂CH̲—CH₃ / NCH₂CH₂CH₃⟩ H₃CCHCH₂), 3.00(N⟨CH₂CH—CH₃ / NCH₂CH₂CH₃⟩ H₃CCHCH̲₂), 3.53(N⟨CH₂CH̲—CH₃ / NCH₂CH₂CH₃⟩ H₃CCHCH₂),

PREPARATION EXAMPLE 18 (Synthesis of derivative 40)

1.60 g of 3'-methylbenzoxazinorifamycin (synthesized by the method described in JP-A-64-006279) was dissolved into 4 ml of N,N-dimethylacetamide, and the mixture was heated up to 50° C. To the mixture were added 0.35 g of morpholine and 0.52 g of manganese dioxide and the reaction was continued at 50° C. for 4 hours. To dilute the reaction mixture, 30 ml of ethanol was added. The solid in the reaction mixture was separated by filtration using diatomaceous earth as a filter aid and the residue on the funnel was rinsed with 30 ml of ethanol. The combined ethanol filtrate and rinse was concentrated to dryness under reduced pressure to give a crude product. The obtained crude product was dissolved into 4 ml of ethyl acetate and the resulting solution was added dropwise to hexane for reprecipitation. The resulting reprecipitated product was purified by preparative layer chromatography using Silica Gel 60, 200×200×2 mm, and chloroform/methanol=98/2 (volume ratio) as solvent. The resulting partially purified product was purified by silica gel column chromatography using 70 g of Wakogel C-200® and chloroform/methanol=98/2 (volume ratio) as eluent. Further, silica gel column chromatography was conducted once more in the same manner as above except for using 50 g of Wakogel C-200®. Fractions containing the desired product were collected and concentrated to dryness under reduced pressure. The yield was 1.40 g.

Thin-layer Chromatography:

Rf 0.46 blue spot (solvent: chloroform/methanol=95/5 volume ratio), Rf 0.33 blue spot (solvent: toluene/tert-butanol=9/1 volume ratio)

¹H-NMR:

The signals derived from the introduced morpholine: 2.83 (NCH₂CH̲₂O), 3.46 (NCH̲₂CH₂O)

PREPARATION EXAMPLE 19 (Synthesis of derivative 43)

1.60 g of 3'-methylbenzoxazinorifamycin was dissolved into 3.35 ml of N,N-dimethylacetamide, and the mixture was heated up to 50° C. To the mixture were added a mixture prepared by suspending 0.61 g of 4-piperidone hydrochloride monohydrate and 0.84 ml of triethylamine in 1 ml of N,N-dimethylacetamide and 0.52 g of manganese dioxide and the reaction was continued at 50° C. for 18 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 500 ml of ethyl acetate. The resulting mixture was washed with 50 ml portions of water 4 times, with 25 ml portions of hydrochloric acid (0.1 mole/l) twice and further with 25 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 40 g of Wakogel C-200® and chloroform as eluent and further by silica gel column chromatography using 30 g of Wakogel C-200® and chloroform/methanol=98/2 (volume ratio) as eluent. The resulting partially purified product was purified by preparative layer chromatography using Silica Gel 60, 200×200×2 mm, chloroform/methanol=95/5 (volume ratio) as solvent. A portion containing the desired product was scraped away and extracted with a solvent and the extract was concentrated to dryness. The yield was 0.26 g.
Thin-layer Chromatography:
Rf 0.52 blue spot (solvent: chloroform/methanol=95/5 volume ratio), Rf 0.25 blue spot (solvent: toluene/tert-butanol=9/1 volume ratio)
$^1$H-NMR:
The signals derived from the introduced 4-piperidone: 1.80, 2.05 (NCH$_2$CH$_2$C=O), 4.00, 5.00 (NCH$_2$CH$_2$C=O)

PREPARATION EXAMPLE 20 (Synthesis of derivative 44)

Into 9 ml of methanol were dissolved 0.69 g of 4-piperidone hydrochloride monohydrate, 0.74 ml of trimethyl orthoformate and 86 mg of p-toluenesulfonic acid monohydrate, and the reaction was conducted at room temperature for 24 hours. The reaction mixture was evaporated under reduced pressure to remove the solvent. The residue was dissolved into 2 ml of N,N-dimethylacetamide and admixed with 1.4 ml of triethylamine to give a solution of 4,4-dimethoxypiperidine.

Into 3.35 ml of N,N-dimethylacetamide was dissolved 1.57 g of benzoxazinorifamycin, and the mixture was heated up to 50° C. To the mixture were added the above-obtained 4,4-dimethoxypiperidine solution and 0.52 g of manganese dioxide, and the reaction was continued 50° C. for 24 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 300 ml of ethyl acetate. The resulting mixture was washed with 100 ml portions of water 3 times and further with 50 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 80 g of Wakogel C-200® and toluene/acetone=3/1 (volume ratio) as eluent. The resulting partially purified product was purified twice by preparative layer chromatography using Silica Gel 60, 200×200×1 mm, toluene/acetone=3/1 (volume ratio) as solvent. The resulting partially purified product was purified by silica gel column chromatography using 80 g of Wakogel C-200® and toluene/acetone=3/1 (volume ratio) as eluent. Fractions containing the desired product were collected and concentrated to dryness under reduced pressure. The yield was 0.48 g.
Thin-layer Chromatography:
Rf 0.66 blue spot (solvent: chloroform/methanol=95/5 volume ratio), Rf 0.33 blue spot (solvent: toluene/tert-butanol=9/1 volume ratio)
$^1$H-NMR:
The signals derived from the introduced 4,4-dimethoxypiperidine: 1.89 (NCH$_2$CH$_2$C), 3.25 (OCH$_3$), 3.56 (NCH$_2$CH$_2$C)

PREPARATION EXAMPLE 21 (Synthesis of derivative 45)

Into 3.26 ml of methanol were dissolved 0.10 g of 4-piperidone hydrochloride monohydrate, 0.36 ml of trimethyl orthoformate and 5 mg of p-toluenesulfonic acid monohydrate, and the reaction was conducted at room temperature for 24 hours. The reaction mixture was evaporated under reduced pressure to remove the solvent. The residue was dissolved into 1 ml of N,N-dimethylacetamide and admixed with 1.5 ml of triethylamine to give a solution of 4,4-dimethoxypiperidine.

Into 0.6 ml of N,N-dimethylacetamide was dissolved 0.26 g of 3'-methylbenzoxazinorifamycin, and the mixture was heated up to 50° C. To the mixture were added the above-obtained 4,4-dimethoxypiperidine solution and 85 mg of manganese dioxide, and the reaction was continued 50° C. for 24 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 300 ml of ethyl acetate. The resulting mixture was washed with 100 ml portions of water 3 times and further with 50 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 2 g of Wakogel C-200® and chloroform as eluent. Fractions containing the desired product were collected and concentrated to dryness. Hexane was added to the residue and the desired product was separated as a precipitate. The yield was 0.15 g.
Thin-layer Chromatography:
Rf 0.63 blue spot (solvent: chloroform/methanol=95/5 volume ratio), Rf 0.33 blue spot (solvent: toluene/tert-butanol=9/1 volume ratio)
$^1$H-NMR:
The signals derived from the introduced 4,4-dimethoxypiperidine: 1.80 (NCH$_2$CH$_2$C), 3.25 (OCH$_3$), 3.56 (NCH$_2$CH$_2$C)

PREPARATION EXAMPLE 22 (synthesis of derivative 46)

Using 0.57 g of 1,4-dioxa-8-azaspiro[4.5]decane instead of N-ethylpeperazine in Preparation Example 1, the reaction was continued for 24 hours under the same condition as in Preparation Example 1. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 1,000 ml of ethyl acetate. The resulting mixture was washed with 100 ml portions of water twice, with 50 ml of a dilute hydrochloric acid (0.1 mole/l) once and further with 50 ml of water once, and the separated organic layer was dried over anhydrous magnesium sulfate. The dried organic layer was evaporated under reduced pressure to remove the solvent to dryness, giving a crude product. The obtained crude product was purified by silica gel column chromatography using 80 g of Wakogel C-200® and chloroform/methanol=50/1 (volume ratio) as eluent and further by silica gel column chromatography using 100 g of Wakogel C-200® and toluene/acetone=3/1 (volume ratio) as eluent. The resulting partially purified product was purified by preparative layer chromatography using Silica Gel 60, 200×200×0.5 mm and toluene/acetone=4/1 (volume ratio) as solvent. A portion containing the desired product was scraped away and extracted with a solvent and the extract was concentrated to dryness. The yield was 0.64 g.

Thin-layer Chromatography:

Rf 0.63 blue spot (solvent: chloroform/methanol=95/5 volume ratio), Rf 0.31 blue spot (solvent: toluene/tert-butanol=9/1 volume ratio)

$^1$H-NMR:

The signals derived from the introduced 1,4-dioxa-8-azaspiro[4.5]decane: 1.80 (NCH$_2$C$\underline{\text{H}}_2$C), 3.66 (NC$\underline{\text{H}}_2$CH$_2$C), 4.02 (OC$\underline{\text{H}}_2$C$\underline{\text{H}}_2$O)

PREPARATION EXAMPLE 23 (Synthesis of derivative 47)

1.60 g of 3'-methylbenzoxazinorifamycin was dissolved into 3.35 ml of N,N-dimethylacetamide, and the mixture was heated up to 50° C. To the mixture were added 0.57 of 1,4-dioxa-8-azaspiro[4.5]decane and 0.52 g of manganese dioxide and the reaction was continued at 50° C. for 41 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 800 ml of ethyl acetate. The resulting mixture was washed with 100 ml portions of water twice, with 50 ml of a dilute hydrochloric acid (0.1 mole/l) once and further with 50 ml of water once, and the separated organic layer was dried over anhydrous magnesium sulfate. The dried organic layer was evaporated under reduced pressure to remove the solvent to dryness, giving a crude product. The obtained crude product was purified by silica gel column chromatography using 80 g of Wakogel C-200® and chloroform/methanol=100/0 (volume ratio) to chloroform/methanol=50/1 (volume ratio) as eluent. The yield was 1.45 g.

Thin-layer Chromatography:

Rf 0.56 blue spot (solvent: chloroform/methanol=95/5 volume ratio), Rf 0.30 blue spot (solvent: toluene/tert-butanol=9/1 volume ratio)

$^1$H-NMR:

The signals derived from the introduced 1,4-dioxa-8-azaspiro[4.5]decane: 1.70 (NCH$_2$C$\underline{\text{H}}_2$C), 3.65 (NC$\underline{\text{H}}_2$CH$_2$C), 4.01 (OC$\underline{\text{H}}_2$C$\underline{\text{H}}_2$O)

PREPARATION EXAMPLE 24 (Synthesis of derivative 48)

Using 0.40 g of N-methylpiperazine instead of morpholine in Preparation Example 18, the reaction was continued for 3.5 hours under the same condition as in Preparation Example 18. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 200 ml of ethyl acetate. The resulting mixture was washed with 20 ml of hydrochloric acid (0.1 mole/l) and further with 20 ml of a saturated solution of sodium chloride, and the separated organic layer was dried over anhydrous magnesium sulfate. The dried organic layer was evaporated under reduced pressure to remove the solvent to dryness, giving a crude product. The obtained crude product was purified by silica gel column chromatography using 50 g of Wakogel C-200® and chloroform/methanol=95/5 (volume ratio) as eluent. The resulting partially purified product was dissolved into 10 ml of ethyl acetate and the solution was added dropwise to 50 ml of hexane to give a precipitate. The precipitate was purified by preparative layer chromatography using Silica Gel 60, 200×200×2 mm and chloroform/methanol=95/5 (volume ratio) as solvent. The partially purified product was purified by silica gel column chromatography using 15 g of Wakogel C-200® and chloroform/toluene=1/1 (volume ratio) to chloroform/toluene/methanol=95/95/5 (volume ratio) as eluent. Fractions containing the desired product were collected and concentrated to dryness, giving the desired product. The yield was 1.21 g.

Thin-layer Chromatography:

Rf 0.20 blue spot (solvent: chloroform/methanol=95/5 volume ratio), Rf 0.02 blue spot (solvent: toluene/tert-butanol=9/1 volume ratio)

$^1$H-NMR:

The signals derived from the introduced N-methylpiperazine: 2.35 (NCH$_3$), 2.56, 2.81 (NCH$_2$C$\underline{\text{H}}_2$NCH$_3$), 3.53 (NC$\underline{\text{H}}_2$CH$_2$NCH$_3$)

PREPARATION EXAMPLE 25 (Synthesis of derivative 49)

0.50 g of 3'-methylbenzoxazinorifamycin was dissolved into 0.84 ml of N,N-dimethylacetamide, and the mixture was heated up to 50° C. To the mixture were added 0.14 g of N-ethylpiperazine and 0.16 g of manganese dioxide and the reaction was continued at 50° C. for 2 hours. To dilute the reaction mixture, 20 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 500 ml of ethyl acetate. The resulting mixture was washed with 50 ml portions of water 3 times, with 15 ml of a dilute hydrochloric acid (0.1 mole/l) once, with 50 ml portions of water twice and further with 50 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was dissolved into 10 ml of ethyl acetate and the resulting solution was added dropwise to hexane for reprecipitation. The obtained precipitate was purified by silica gel column chromatography using 80 g of Wakogel C-200® and toluene/acetone=3/1 (volume ratio) to chloroform/methanol=95/5 (volume ratio) as eluent. Fractions containing the desired product were collected and concentrated to dryness, giving the desired product. The yield was 0.24 g.

Thin-layer Chromatography:

Rf 0.43 blue spot (solvent: chloroform/methanol=95/5 volume ratio), Rf 0.04 blue spot (solvent: toluene/tert-butanol=9/1 volume ratio)

$^1$H-NMR:

The signals derived from the introduced N-ethylpiperazine: 1.26 (NCH$_2$C$\underline{\text{H}}_3$), 2.48 (NC$\underline{\text{H}}_2$CH$_3$), 2.60 (NCH$_2$C$\underline{\text{H}}_2$NCH$_2$CH$_3$), 3.54 (NC$\underline{\text{H}}_2$CH$_2$NCH$_2$CH$_3$)

PREPARATION EXAMPLE 26 (Synthesis of derivative 50)

Using 0.51 g of N-isopropylpiperazine instead of 1,4-dioxa-8-azaspiro[4.5]decane in Preparation Example 23, the reaction was continued at 50° C. for 5.5 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 1,000 ml of ethyl acetate. The resulting mixture was washed with 50 ml of hydrochloric acid (0.1 mole/l) once, with 150 ml of water once and further with 50 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 80 g of Wakogel C-200® and toluene/tert-butanol=4/1 (volume ratio) to chloroform/methanol=95/5 (volume ratio) as eluent. Fractions containing the desired product were collected and concentrated to dryness, giving the desired product. The yield was 1.66 g.

Thin-layer Chromatography:

Rf 0.30 blue spot (solvent: chloroform/methanol=95/5 volume ratio), Rf 0.08 blue spot (solvent: toluene/tert-butanol=9/1 volume ratio)

$^1$H-NMR:

The signals derived from the introduced N-isopropylpiperazine; 1.01 (NCH(C$\underline{H}_3$)$_2$), 2.67 (NCH$_2$C$\underline{H}_2$NCH), 2.81 (NC$\underline{H}$(CH$_3$)$_2$), 3.52 (NC$\underline{H}_2$CH$_2$NCH)

PREPARATION EXAMPLE 27 (Synthesis of derivative 51)

Using 0.51 g N-propylpiperazine instead of morpholine in Preparation Example 18, the reaction was continued at 50° C. for 6 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 500 ml of ethyl acetate. The resulting mixture was washed with 20 ml of hydrochloric acid (0.1 mole/l) once and further with 20 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was dissolved into 15 ml of ethyl acetate and the resulting solution was added dropwise to 150 ml of hexane for reprecipitation. The obtained precipitate was purified by silica gel column chromatography using 60 g of Wakogel C-200® and chloroform/methanol=95/5 (volume ratio) as eluent. Fractions containing the desired products were collected and concentrated to dryness, giving the desired product. The yield was 1.52 g.

Thin-layer Chromatography:

Rf 0.33 blue spot (solvent: chloroform/methanol=95/5 volume ratio), Rf 0.13 blue spot (solvent: toluene/tert-butanol=9/1 volume ratio)

$^1$H-NMR:

The signals derived from the introduced N-propylpiperazine: 0.95 (NCH$_2$CH$_2$C$\underline{H}_3$), 1.56 (NCH$_2$C$\underline{H}_2$NCH$_3$), 2.36 (NC$\underline{H}_2$CH$_2$CH$_3$), 2.59 (NCH$_2$C$\underline{H}_2$NCH$_2$) 3.53 (NC$\underline{H}_2$CH$_2$NC$\underline{H}_2$)

PREPARATION EXAMPLE 28 (Synthesis of derivative 52)

Using 0.57 g of N-butylpiperazine instead of morpholine in Preparation Example 18, the reaction was continued at 50° C. for 8.5 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 1,000 ml of ethyl acetate. The resulting mixture was washed with 100 ml portions of water twice, with 50 ml of hydrochloric acid (0.1 mole/l) once and further with 100 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 75 g of Wakogel C-200® and chloroform/methanol=95/5 (volume ratio) as eluent. Fractions containing the desired product were collected and concentrated to dryness, giving the desired product. The yield was 1.63 g.

Thin-layer Chromatography:

Rf 0.40 blue spot (solvent: chloroform/methanol=95/5 volume ratio), Rf 0.21 blue spot (solvent: toluene/tert-butanol=9/1 volume ratio)

$^1$H-NMR:

The signals derived from the introduced N-butylpiperazine: 0.93 (NCH$_2$CH$_2$CH$_2$C$\underline{H}_3$), 1.37 (NCH$_2$CH$_2$C$\underline{H}_2$CH$_3$), 1.51 (NCH$_2$C$\underline{H}_2$CH$_2$CH$_3$), 2.40 (NC$\underline{H}_2$CH$_2$CH$_2$C$\underline{H}_3$), 2.58 (NCH$_2$C$\underline{H}_2$NCH$_2$), 3.52 (NC$\underline{H}_2$CH$_2$NCH$_2$)

PREPARATION EXAMPLE 29 (Synthesis of derivative 53)

Using 0.50 g of N-(2-propenyl)piperazine instead of 1,4-dioxa-8-azaspiro[4.5]decane in Preparation Example 23, the reaction was continued at 50° C. for 7.5 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 1,000 ml of ethyl acetate. The resulting mixture was washed with 50 ml of hydrochloric acid (0.1 mole/l) once, with 150 ml of water once and further with 50 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 90 g of Wakogel C-200® and chloroform/methanol=95/5 (volume ratio) as eluent. Fractions containing the desired product were collected and concentrated to dryness, giving the desired product. The yield was 1.02 g.

Thin-layer Chromatography:

Rf 0.37 blue spot (solvent: chloroform/methanol=95/5 volume ratio), Rf 0.15 blue spot (solvent: toluene/tert-butanol=9/1 volume ratio)

$^1$H-NMR:

The signals derived from the introduced N-(2-propenyl) piperazine: 2.60 (NCH$_2$CH$_2$NCH$_2$), 2.81 (NCH$_2$CH=CH$_2$), 3.53 (NCH$_2$CH$_2$NCH$_2$), 5.00, 5.21 (NCH$_2$CH=C$\underline{H}_2$), 5.85 (NCH$_2$C$\underline{H}$=CH$_2$)

PREPARATION EXAMPLE 30 (Synthesis of derivative 54)

Using 0.51 g of 1,2,6-trimethylpiperazine instead of 1,4-dioxa-8-azaspiro[4.5]decane in Preparation Example 23, the reaction was continued at 50° C. for 41 hours. To dilute the reaction mixture, 30 ml of ethyl acetate was added. The solid in the reaction mixture was separated by filtration using diatomaceous earth as a filter aid and the residue on the funnel was rinsed with 50 ml of ethyl acetate. The combined ethyl acetate filtrate and rinse was diluted with 800 ml of ethyl acetate. The resulting mixture was washed with 100 ml portions of water twice, with 50 ml of hydrochloric acid (0.1 mole/l) once and further with 50 ml portions of a saturated solution of sodium chloride twice, and the separated organic layer was dried over anhydrous magnesium sulfate. The dried organic layer was evaporated under reduced pressure to remove the solvent to dryness, giving a crude product. The obtained crude product was purified by silica gel column chromatography using 90 g of Wakogel C-200® and chloroform/methanol=98/2 (volume ratio) as eluent and further by silica gel column chromatography using 30 g of Wakogel C-200® and chloroform/methanol=99/1 (volume ratio) as eluent. The resulting partially purified product was purified by preparative layer chromatography using Silica Gel 60, 200×200×0.25 mm, chloroform/methanol=95/5 (volume ratio) as solvent. A portion containing the desired product was scraped away and extracted with a solvent and the extract was concentrated to dryness. The yield was 0.29 g.

Thin-layer Chromatography:

Rf 0.32 blue spot (solvent: chloroform/methanol=95/5 volume ratio), Rf 0.06 blue spot (solvent: toluene/tert-butanol=9/1 volume ratio)

$^1$H-NMR:

The signals derived from the introduced 1,2,6-trimethylpiperazine: 1.21, 1.22 (NCH$_2$CH(C$\underline{H}_3$)), 2.32 (NC$\underline{H}_3$), 2.90 (NCH$_2$C$\underline{H}$(CH$_3$)), 3.77 (NC$\underline{H}_2$CH(CH$_3$))

PREPARATION EXAMPLE 31 (Synthesis of derivative 55)

Into 10 ml of methanol was dissolved 0.46 of derivative 25 at 50° C., and 0.57 ml of a 30% aqueous solution of hydrogen peroxide was added thereto. The reaction was conducted at 50° C. for 7 hours, at 40° C. for 15 hours, at 50° C. for 7 hours and at 30° C. for 15 hours. After completion of the reaction, the reaction mixture was concentrated to about 4 ml, to which 20 ml of ethyl acetate and 20 ml of an aqueous solution of sodium chloride were added. The organic layer was separated from the aqueous layer and washed with 10 ml portions of water twice. In that case, a tar-like material was separated out. The tar-like material was dissolved with a mixture of chloroform and methanol and combined with the organic layer. The organic layer was concentrated to dryness. The resulting residue was dissolved into chloroform and an insoluble material was filtered off. The chloroform solution was concentrated under reduced pressure to dryness. The obtained crude product was purified by preparative layer chromatography using Silica Gel 60, 200×200×2 mm and chloroform/methanol=8/2 (volume ratio) as solvent and then by the same preparative layer chromatography as above except that the solvent was changed to chloroform/methanol=9/1 (volume ratio). A portion containing the desired product was scraped away and eluted with a solvent. The eluate was concentrated to dryness. The yield was 0.29 g.

Thin-layer Chromatography:

Rf 0.31 blue spot (solvent: chloroform/methanol=8/2 volume ratio), Rf 0.02 blue spot (solvent: toluene/tert-butanol=1/1 volume ratio)

The mass spectrum of the above-obtained compound was measured by a fast atom bombardment. In the spectrum, a peak which was larger than that of the starting material by 16 mass units was observed, which reveals that the compound is a compound having mass equal to that of the compound which is obtained by introducing oxygen into the starting material, that is, N-oxide compound. From these results, it was confirmed that of the compound of this Preparation Example is the N-oxide compound of derivative 25.

The present invention provides the new medicine, the effective ingredient of which is rifamycin derivatives or their physiologically acceptable salts, for diseases caused by the infection of *Helicobacter pylori*.

What is claimed is:

1. A method for treating a digestive organ disease caused by the infection of Helicobacter, comprising administering a rifamycin derivative expressed by the formula (I), or a physiologically acceptable salt thereof:

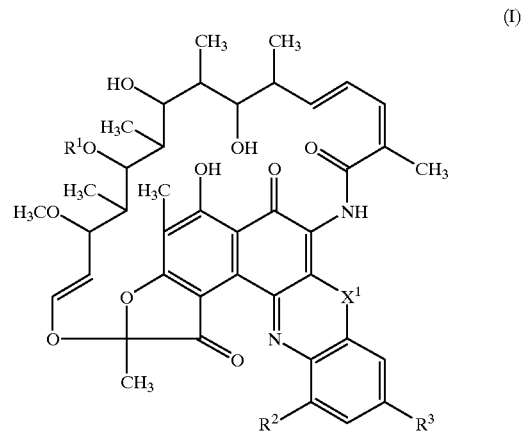

wherein $X^1$ represents an oxygen atom or a sulfur atom, $R^1$ represents an acetyl group or a hydrogen atom, $R^2$ represents a hydroxy group, a hydrogen atom, or an alkyl group having 1 to 3 carbon atoms, $R^3$ represents a group expressed by the formula:

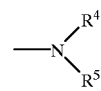

wherein $R^4$ and $R^5$ are the same or different and each is an alkyl group having 1 to 3 carbon atoms or

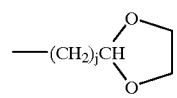

in which j represents an integer between 1 and 3; or a group expressed by the formula:

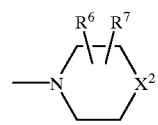

wherein $R^6$ and $R^7$ are the same or different and each is a hydrogen atom or an alkyl group having 1 to 3 carbon atoms, $X^2$ represents an oxygen atom, a sulfur atom, a carbonyl group,

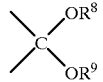

in which $R^8$ and $R^9$ are the same or different and each is a hydrogen atom, an alkyl group having 1 to 3 carbon atoms, or $R^8$ and $R^9$, in combination with each other, represent —(CH$_2$)$_k$— in which k represents an integer between 1 and 4, or

in which m represents 0 or 1, $R^{10}$ represents a hydrogen atom, an alkyl group having 1 to 6 carbon atoms or —(CH$_2$)$_n$X$^3$ in which n represents an integer between 1 and 4, and $X^3$ represents an alkoxy group having 1 to 3 carbon atoms, a vinyl group, an ethynyl group, or

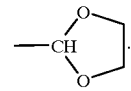

* * * * *